US008501721B2

(12) United States Patent
Fukuoka et al.

(10) Patent No.: US 8,501,721 B2
(45) Date of Patent: Aug. 6, 2013

(54) POSTPRANDIAL HYPERGLYCEMIA-IMPROVING AGENT

(75) Inventors: Daisuke Fukuoka, Haga-gun (JP); Kohjiro Hashizume, Haga-gun (JP); Akira Shimotoyodome, Haga-gun (JP)

(73) Assignee: Kao Corporation, Tokyo (JP)

( * ) Notice: Subject to any disclaimer, the term of this patent is extended or adjusted under 35 U.S.C. 154(b) by 158 days.

(21) Appl. No.: 13/144,551

(22) PCT Filed: Jan. 15, 2010

(86) PCT No.: PCT/JP2010/050751
§ 371 (c)(1),
(2), (4) Date: Jul. 14, 2011

(87) PCT Pub. No.: WO2010/082690
PCT Pub. Date: Jul. 22, 2010

(65) Prior Publication Data
US 2011/0275605 A1 Nov. 10, 2011

(30) Foreign Application Priority Data

Jan. 16, 2009 (JP) .................................. 2009-007797
Dec. 1, 2009 (JP) .................................. 2009-273499

(51) Int. Cl.
*A61K 31/56* (2006.01)
(52) U.S. Cl.
USPC ........................................................ 514/182
(58) Field of Classification Search
USPC ........................................................ 514/182
See application file for complete search history.

(56) References Cited

U.S. PATENT DOCUMENTS

| 4,707,472 | A | 11/1987 | Inagaki et al. | |
|---|---|---|---|---|
| 2007/0196435 | A1* | 8/2007 | Higuchi et al. | 424/439 |
| 2010/0035851 | A1 | 2/2010 | Tanaka et al. | |
| 2010/0056487 | A1 | 3/2010 | Findeis et al. | |

FOREIGN PATENT DOCUMENTS

| CN | 1859917 A | 11/2006 |
|---|---|---|
| CN | 101277705 A | 10/2008 |
| EP | 1795200 A1 | 6/2007 |
| EP | 1930014 A1 | 6/2008 |
| JP | 1986-106512 A | 5/1986 |
| JP | 62-277326 A | 12/1987 |
| JP | 2005-068132 A | 3/2005 |
| WO | WO 2008/130449 A2 | 10/2008 |

OTHER PUBLICATIONS

Notification of First Office Action for Chinese Patent Application No. 201080004739.X, mailed Sep. 18, 2012, Patent Office of the People's Republic of China, Beijing, China.

Jin, He et al., "Progress of the Treatment for Postprandial Hyperglycemia by Medicine," Pharm. J. of Chinese People's Liberation Army 17(4):203-207 (Aug. 2001), General Logistics Department of the Ministry of Health of the People's Republic of China, China Academic Journal of Electronic Publishing House, China.

Xiao, J. et al., "International Diabetew Federation, Guidelines of controlling postprandial blood glucose level," Drug Evaluation 5(1):39-52 (Dec. 2008), China Academic Journal of Electronic Publishing House, China.

Meng, B., "Risk of postprandial hyperglycemia and treatment," Chinese J. of Misdiagnostics 3(11):1650-1651 (Nov. 2003), Ministry of Health of the People's Republic of China, China Academic Journal Electronic Publishing House, China.

International Search Report (ISR) for PCT/JP2010/050751, I.A. fd: Jan. 15, 2010, mailed Mar. 18, 2010 from the European Patent Office, Rijswijk, Netherlands.

International Preliminary Report on Patentability (IPRP), Chapter I of the Patent Cooperation Treaty, including the Written Opinion for PCT/JP2010/050751, I.A. fd: Jan. 15, 2010, issued Jul. 19, 2011 from the International bureau of WIPO, Geneva, Switzerland.

Tominaga, M et al., "Impaired glucose tolerance is a risk facter for cardiovascular disease, but not impaired fasting glucose. The Funagata Diabetes Study," Diabetes Care, Jun. 1999; 22: 920-924, Am. Diabetes Assoc., Alexandria, VA.

DECODE Study Group; on behalf of the European Eidabetes Epidemiology Group, "Glucose Tolerance and Cardiovascular Mortality: Comparison of Fasting and 2-Hour Diagnostic Criteria," Arch Intern Med, Feb. 2001; 161: 397-405, Am. Medical Assoc., Chicago, IL.

Risso, A, et al., "Intermittent high glucose enhanes apoptosis in human umbilical vein endothelial cells in culture," Am J Physiol Endocrinol Metab, Nov. 2001; 281: E924-E930, Am. Physiological Soc., Bethesda, MD.

Sultana, S et al., "Inhibition of benzoyl peroxide and ultraviolet-B radiation induced oxidative stress and tumor promotion markers by cycloartenol in murin skin," Redox Rep. Jan. 2003; 8(2): 105-112, W. S. Maney and Son, Leeds, UK.

Ahumada, C et al., "The effects of a tritepene fraction isolated from *Crataegus monogyna* Jacq. on different acute inflammation models in rats and mice. Leucocyte migration and phospholipase $A_2$ inhibition," J Pharm Pharmacol, Mar. 1997, 49(3): 329-331, Pharmaceutical Press, London, England.

Kiribuchi, M et al., "Hypocholesteolemic effect of triterpene alcohols with soysterol on plasma cholesteral in rats," J Nutr Sci Vitaminol (Tokyo), Feb. 1983; 29(1): 35-43, University of Tokyo Press, Tokyo, Japan.

Cavalot, F et al.,"Postpranial blood glucose is a stronger predictor of cardiovascular events than fasting blood glucose in type 2 diabetes mellitus, particularly in women: lessons from the Sari Luigi Gonzaga Diabetes Study," J Clin Endocrine! Metab 91:813-819 (Mar. 2006), Endocrine Society, Chevy Chase, MD.

* cited by examiner

*Primary Examiner* — Rei-tsang Shiao
(74) *Attorney, Agent, or Firm* — Sterne, Kessler, Goldstein & Fox P.L.L.C.

(57) ABSTRACT

A postprandial hyperglycemia-improving agent, the agent is highly safe and exhibits excellent effects of inhibiting the postprandial increase of blood glucose. The postprandial hyperglycemia-improving agent comprises a cycloartenol or a derivative thereof as an active ingredient.

14 Claims, No Drawings

POSTPRANDIAL HYPERGLYCEMIA-IMPROVING AGENT

FIELD OF THE INVENTION

The present invention relates to postprandial hyperglycemia-improving agent, which inhibits the postprandial increase of blood glucose.

BACKGROUND OF THE INVENTION

A postprandial excessive blood glucose symptom is defined as the condition where the postprandial glucose level in blood increases beyond the normal range of glucose (for example, 140 mg or higher as the blood glucose level of two hours after eating), and means that the blood glucose level after ingestion of carbohydrates becomes high even for healthy people who are not diabetes patients and borderline diabetes patients. Thus, the postprandial excessive blood glucose symptom is conceptually different from an excessive casual blood glucose symptom in which the fasting blood glucose level is constantly higher than the normal level range due to diabetes.

After eating, in particular, after the ingestion of a diet containing carbohydrates, the increase of the blood glucose level generally induces the promotion of insulin secretion. Insulin mediates its action in the muscle, the liver, the fat tissue or the like, and inhibits the rapid postprandial increase of a blood glucose level. However, prolonged insulin secretion due to a continuous hyperglycemia condition leads to reduction of insulin sensitivity (insulin resistance) in target organs for insulin such as the muscle, and further, a larger amount of insulin is secreted from pancreas. Then, exhaustion of the pancreas finally occurs, and secretion of insulin from pancreatic β-cells lowers. However, each target organ for insulin remains in a state of increased insulin resistance. Thus, as is known, malfunction of the insulin action mechanism results in obesity or type II diabetes (hyperglycemia).

Further, in recent years, it has been reported that postprandial excessive blood glucose is an independent risk factor of a cardiovascular event (Non-Patent Documents 1 and 2), and it has been reported that although there is weak correlation between fasting hyperglycemia and a probability of death from a cardiovascular disease, however there is strong correlation between hyperglycemia of patients who show 200 mg/dL or higher in the level of two hours after eating in the oral glucose tolerance test (OGTT) and a probability of death from a cardiovascular disease (Non-Patent Document 2). Further, it has also been reported that when vascular endothelial cells are cultured in a hyperglycemia condition, apoptosis of the cells occurs more frequently in an intermittent hyperglycemia condition than in a continuous hyperglycemia condition (Non-Patent Document 3).

Accordingly, the postprandial excessive blood glucose symptom is not only an inducement of type II diabetes and obesity, but also a cause or a precipitating factor of various diseases such as arteriosclerosis and further hyperlipidemia, hence, prevention of the postprandial excessive blood glucose symptom is useful for prophylaxis and treatment of those diseases.

An α-glycosidase inhibitor, a rapid-acting insulin secretion accelerator, and the like are known as therapeutic agents for postprandial excessive blood glucose, and they are mainly used for severe patients in medical institutions. In contrast, a nonpharmacological therapy, which is a collective name for improvement in lifestyle habit, such as a diet therapy, an exercise therapy, and limitation of alcohol drinking and smoking, is widely applicable to subjects, from prophylaxis for normal subject to treatment of severe patients exhibiting an excessive blood glucose symptom.

Although, many of the drugs used for improving postprandial excessive blood glucose are satisfactory in their effectiveness at present, however on the other hand, concerns about prolonged use of those drugs are pointed out, because, for example, the drugs have caused adverse effects such as abdominal bloating, flatulence, flatus increase, loose stool, diarrhea, abdominal pain, and hepatic dysfunction. In addition, long-term implementation of a general therapy such as a diet therapy and an exercise therapy involves extreme difficulties. Therefore, there has been demanded a material for inhibiting the postprandial increase of blood glucose, the material having little adverse effects, being ingestible on a daily basis, and being derived from naturally occurring substances.

From the foregoing, materials derived from food have been actively searched for the purpose of inhibiting the rapid postprandial increase of blood glucose, and as a result, many active ingredients exhibiting an action of inhibiting the increase of blood glucose have been isolated and identified. Although there have been discovered foods or active ingredients thereof which seem to exhibit an action of inhibiting the increase of blood glucose, these effectiveness has not always been satisfactory.

Meanwhile, cycloartenol is biosynthetic precursor of plant sterols, and are triterpene alcohols which are distributed in latex of plants belonging to the family Euphorbiaceae, rice bran, rapeseeds, and the like.

It has been reported that cycloartenol mediates actions such as inhibition of oncogenesis promotion, an anti-inflammatory action, a cholesterol lowering action, and an action of promoting adiponectin secretion (Patent Document 1 and Non-Patent Documents 4 to 6). In addition, it has been reported that ferulic acid esters of cycloartenol exhibit an action of improving a brain function, an action of controlling an autonomic nerve function, and the like (Patent Documents 2 and 3).

However, there has been no report on the relationship between cycloartenol and postprandial excessive blood glucose.

PRIOR ART DOCUMENTS

Patent Documents

[Patent Document 1] JP-A-2005-68132
[Patent Document 2] JP-A-62-277326
[Patent Document 3] JP-A-61-106512

Non-Patent Documents

[Non-Patent Document 1] Diabetes Care. 1999; 22: 920-924
[Non-Patent Document 2] Arch Intern Med. 2001; 161: 397-405
[Non-Patent Document 3] Am J Physiol Endocrinol Metab. 2001; 281: E 924-930
[Non-Patent Document 4] Sultana S. et al., 2003, Redox Rep., 8, 105-12
[Non-Patent Document 5] Ahumada C. et al., 1997, J Pharm Pharmacol., 49, 329-31
[Non-Patent Document 6] Kiribuchi M. et al., 1983, J Nutr Sci Vitaminol (Tokyo), 29, 35-43

SUMMARY OF THE INVENTION

The present invention provides a postprandial hyperglycemia-improving agent containing a cycloartenol or a derivative thereof as an active ingredient.

The present invention also provides a pharmaceutical composition for improving postprandial hyperglycemia, containing a cycloartenol or a derivative thereof, and a pharmaceutically acceptable carrier.

The present invention also provides a method of improving postprandial hyperglycemia, containing administering or ingesting a cycloartenol or a derivative thereof.

The present invention also provides a non-therapeutic use of a cycloartenol or a derivative thereof for improving postprandial hyperglycemia.

The present invention also provides a cycloartenol or a derivative thereof for preventing and/or improving a disease caused by postprandial excessive blood glucose.

DETAILED DESCRIPTION OF THE INVENTION

The present invention relates to providing a postprandial hyperglycemia-improving agent, which is highly safe and excellent in an effect of inhibiting the postprandial increase of blood glucose.

The inventors of the present invention have studied materials capable of controlling postprandial excessive blood glucose, and found out that cycloartenol exhibits an excellent action of inhibiting the postprandial increase of blood glucose.

The postprandial hyperglycemia-improving agent of the present invention may control blood glucose level that increases after eating within a favorable range, hence, the use of the agent enables to prevent diabetes (hyperglycemia), arteriosclerosis, obesity and the signs thereof, and improvement in the physical conditions.

In the present invention, inhibiting the postprandial increase of blood glucose, in another word, the terms "improving the postprandial hyperglycemia" means suppressing a symptom in which the blood glucose level after ingestion of carbohydrates increases, that is, suppressing a postprandial excessive blood glucose symptom, and is conceptually different from "improvement of hyperglycemia" in which a patient, whose fasting blood glucose level is constantly higher than the normal level range due to diabetes, gradually control the glucose level by prolonged ingestion.

In addition, the term "non-therapeutic" in the present invention refers to a concept that does not include medical practice (medical treatment of a human body or an animal body through therapy).

In the present invention, cycloartenol refers to triterpene alcohols represented by the following general formula (1) and contained in rice bran, *Avena sativa* L., coconut palm, soybean, olive, rapeseed, sesame, cocoa, or the like.

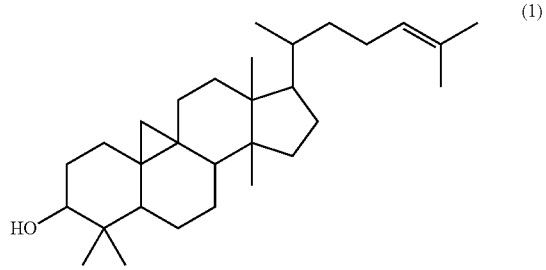

(1)

As cycloartenol derivatives, esters such as fatty acid esters, ferulic acid esters, and cinnamic acid esters of cycloartenol and glycosides such as saponin are exemplified. Among these, ferulic acid esters of cycloartenol are preferred.

Those cycloartenol or derivatives thereof may be obtained by known organic chemical synthetic method, by extraction from a naturally occurring substance and callus each containing the cycloartenol, derivatives or precursors thereof, or by combination with an organic chemical synthetic method or a hydrolysis method, if necessary.

As the naturally occurring substance and callus each containing cycloartenol, derivatives or precursors thereof, rice bran, *Avena sativa* L., coconut palm, soybean, olive, rapeseed, sesame, and cocoa are exemplified. In the present invention, in particular, those extracted from rice bran are preferably used. It should be noted that rice bran refers to portions other than an endosperm (an episperm, a pericarp, a starch layer, and a germ), which are removed when brown rice is subjected to grain polishing, and they may be a mixture thereof or any of isolated product obtained from them.

Those cycloartenol or derivatives thereof obtained by the above synthesis or extraction may be roughly purified products or further purified products, which are obtained by subjecting the synthesized product or the extract to a suitable combination of known separation and purification methods, as long as the cycloartenol or derivatives thereof meet an acceptable standard for a drug or food and exhibit the effect of the present invention.

Extraction may be carried out using, in addition to solvent extraction involving performing immersion in a solvent at room temperature or in a condition of heating or involving using an extractor such as a Soxhlet extractor, a method for extraction using a distillation method such as steam distillation, a supercritical extraction method using carbon dioxide in a supercritical condition, and a squeezing method involving squeezing, to provide an extract.

An extraction solvent used for solvent extraction includes, for example, alcohols such as methanol, ethanol, propanol, and butanol; polyols such as ethylene glycol, propylene glycol, and butylene glycol; ketones such as acetone and methyl ethyl ketone; esters such as methyl acetate and ethyl acetate; chained or cyclic ethers such as tetrahydrofuran and diethyl ether; polyethers such as polyethylene glycol; halogenated hydrocarbons such as dichloromethane, chloroform, and carbon tetrachloride; hydrocarbons such as hexane, cyclohexane, and petroleum ether; aromatic hydrocarbons such as benzene and toluene; pyridines; supercritical carbon dioxide; and fats and oils, wax, and other oils. Those solvents may be used alone or in a combination of two or more kinds, and the solvent extraction may be repeated by changing the solvent. Of those solvents, lipophilic solvents such as hydrocarbons are preferably used, and hexane is more preferably used.

The extraction is preferred to be carried out by using 1 to 50 parts by weight of a solvent with respect to 1 part by weight of a rice bran freeze-dried product and subjecting to immersion or reflux under heating at 3° C. to 100° C. for several hours to several weeks.

Further, the means for purifying extracts include organic solvent precipitation, centrifugation, use of an ultrafiltration membrane, high-performance liquid chromatography, and column chromatograph.

In the present invention, extracts containing cycloartenol or derivatives thereof may be used without further treatment, and a rice bran extract may be used, for example. The extract may be used as a diluted liquid obtained by diluting the liquid of the extract with a suitable solvent, or as a concentrated extract, a dried powder, or paste may be used. Specific examples thereof include a rice bran oil, and an ingredient enriched oil obtained by subjecting the rice bran oil to an enzymatic treatment, followed by distillation and deacidification. Alternatively, a commercially available preparation containing cycloartenol or derivatives thereof may be used.

As shown in the examples described below, cycloartenol exhibits an action of significantly inhibiting the excessive postprandial increase of blood glucose. Accordingly, cycloartenol or derivatives thereof may be used as postprandial hyperglycemia-improving agent, and may be used as an agent for lowering the risk of the onset of postprandial excessive blood glucose and diseases caused thereby, or as an agent for preventing, improving, or treating the postprandial excessive blood glucose and diseases caused thereby (hereinafter, referred to as "postprandial hyperglycemia-improving agent or the like"), the diseases including insulin resistance caused by an increase of biological oxidative stress, and various lifestyle-related diseases such as obesity, arteriosclerosis, diabetes, and hyperlipidemia, and in addition, the cycloartenol or derivatives thereof may be used for producing those agents. In this case, in the postprandial hyperglycemia-improving agent or the like, there may be used the cycloartenol or derivatives thereof alone, or in addition to them, there may be used acceptable substances such as a carrier being selected appropriately as needed, which is acceptable for product, as described below, to be mixed with. It should be noted that the preparation may be produced by an ordinary method depending on the object substances that have to be mixed.

The content of cycloartenol or derivatives thereof in the postprandial hyperglycemia-improving agent or the like is generally 0.1 to 100 weight %, preferably 1 to 100 weight %, or more preferably 10 to 100 weight %.

The postprandial hyperglycemia-improving agent or the like may be used for adding, as an active ingredient, into a drug for a human being or an animal, a quasi drug, a food, or a feed, wherein the active agent exerts, for example, an effect of lowering the risk of the onset of postprandial excessive blood glucose and diseases caused thereby, or an effect of preventing, improving, or treating the postprandial excessive blood glucose and diseases caused thereby, the diseases including insulin resistance caused by an increase of biological oxidative stress, and various lifestyle-related diseases such as obesity, arteriosclerosis, diabetes, and hyperlipidemia.

In addition, the postprandial hyperglycemia-improving agent or the like is applicable to a food, a functional food, a food for a sick person, a food for specified health use or the like, each of them, if necessary, being labeled to inform of having an action of inhibiting the increase of blood glucose and its use for preventing or improving postprandial excessive blood glucose, which are prepared following the concept for providing physiological functions for promoting the lowering of the risk of the onset of postprandial excessive blood glucose and diseases caused thereby, or of promoting the prevention, improvement or treatment of the postprandial excessive blood glucose and diseases caused thereby. Such diseases include, for example, insulin resistance caused by an increase of biological oxidative stress, and various lifestyle-related diseases such as obesity, arteriosclerosis, diabetes, and hyperlipidemia.

When the postprandial hyperglycemia-improving agent or the like of the present invention is used as an active ingredient in a drug, examples of the administration form include oral administration of a tablet, a capsule, a granule, a powder, a syrup, or the like, or parenteral administration of an injection, a suppository, an inhalant, a transdermal drug, an external drug, or the like.

In order to prepare those pharmaceutical preparations in various formulations, the postprandial hyperglycemia-improving agent or the like of the present invention may be used alone, or may be used in appropriate combination with other pharmaceutically acceptable excipient, binder, expander, disintegrant, surfactant, lubricant, dispersant, buffer, preservative, savoring agent, fragrance, coating, carrier, diluent, and the like.

Of these administration forms, oral administration is preferred. The content of the cycloartenol or derivatives thereof in a preparation for oral administration containing the postprandial hyperglycemia-improving agent or the like is generally 0.01 to 100 weight %, preferably 0.1 to 100 weight %, or more preferably 1 to 100 weight %.

When the postprandial hyperglycemia-improving agent or the like of the present invention is used as an active ingredient in a food, examples of the form of the food include various foods such as breads, cakes, noodles, confectioneries, jellies, frozen foods, ice creams, dairy products and beverages, as well as the same forms as the above-mentioned forms of the preparations for oral administration (a tablet, a capsule, a syrup, or the like).

In order to prepare those foods in various forms, the postprandial hyperglycemia-improving agent or the like may be used alone, or may be used in appropriate combination with other food materials, a solvent, a softener, an oil, an emulsifier, an antiseptic, a fragrance, a stabilizer, a colorant, an antioxidant, a humectant, a thickener, and the like. The content of the cycloartenol or derivatives thereof in those foods containing the postprandial hyperglycemia-improving agent or the like of the present invention is preferably 0.01 to 100 weight %, more preferably 0.1 to 100 weight %, or even more preferably 1 to 100 weight %.

The amount for administration or ingestion of the above-mentioned preparations may vary depending on the condition, body weight, sex, and age of a patient or other factors, the amount for oral administration or ingestion per adult per day is, in terms of cycloartenol, preferably 50 µg to 500 mg, particularly preferably 75 µg to 100 mg, more preferably 100 µg to 20 mg, or even more preferably 150 µg to 5 mg.

Further, the postprandial hyperglycemia-improving agent or the like of the present invention is administered or ingested preferably during or before food intake, or particularly preferably 5 minutes to 30 minutes before food intake or feed intake.

The subjects to be administered may include, in addition to ordinary normal people, borderline diabetes patients and diabetes patients. For the former an effect of preventing diabetes may be expected, and for the latter an effect of improving diabetes may be expected.

EXAMPLE

Example 1

Preparation of Cycloartenol

"ORYZA TRITERPENOID-P" (manufactured by Oryza Oil & Fat Chemical Co., Ltd.) was subjected to separation and purification. As a result, purified cycloartenol and purified 24-methylenecycloartanol were obtained. It should be noted that the product was produced by powdering of triterpenoid obtained from hydrolysis of rice bran and rice germ derived from *Oryza sativa* Linne seeds.

Specifically, 5 g of "ORYZA TRITERPENOID-P" were fractionated by silica gel column chromatography (developing solvent: hexane/ethyl acetate=9/1) to yield 3.93 g of a fraction containing cycloartenol and 24-methylenecycloartanol. Then, 1.4 g of the fraction were fractionated by HPLC (developing solvent: methanol/acetonitrile/tetrahydrofuran/water=15/2/2/1) using ODS column (Inertsil ODS-3: GL Sciences). As a result, 480 mg of purified cycloartenol product and 764 mg of purified 24-methylenecycloartanol were obtained.

(1) Test Example 1

Preparation of Sample

To white rice (Koshihikari produced in Tochigi prefecture), water (1.5 times equivalent to the volume of the white rice) was added to allow the rice to absorb the water for 30 minutes. Then, the rice was cooked with a rice cooker (ZOJIRUSHI microcomputer-controlled rice cooker NS-KG05, manufactured by Zojirushi Corporation). Water and triolein (manufactured by Sigma-Aldrich Corporation) were added to the cooked rice, followed by homogenization until the mixture was sufficiently homogenized, thereby yielding a sample for administration. The sample for administration was orally probe-administered to a group at 2 mg of white rice per g body weight and 1.5 µg of triolein per g body weight (the group as a control group). Each of the purified cycloartenol produced in Example 1 described above was added to a sample for administration (dissolved in triolein). Each of the resultants was orally probe-administered to a group at 2 mg of white rice per g body weight, 1.5 µg of triolein per g body weight, and 0.075 µg, or 0.15 µg, of cycloartenol equivalent per g body weight (the groups as Test group 1 and 2). Further, purified 24-methylenecycloartanol was added to a sample for administration (dissolved in triolein). The resultant was orally probe-administered to a group at 2 mg of white rice per g body weight, 1.5 µg of triolein per g body weight, and 0.15 µg of 24-methylenecycloartanol equivalent per g body weight (the group as Comparative group).

8-week old male Wistar rats (supplied by Japan SLC Inc.), after 15 hours of fasting, were divided into groups each consisting of 10 rats with their body weight being almost the same between the groups. Immediately after the administration to each group, blood sample was collected from tail vein sequentially. The blood sample was measured for its blood glucose level by using ACCU-CHEK AVIVA (manufactured by Roche Diagnostics GmbH) to calculate the maximum increase of blood glucose.

(2) Test Results

Table 1 shows the results of the test. Results are represented as average±standard error, and statistical significant differences between groups were determined by the Dunnett's test with respect to the control group (*p <0.05).

TABLE 1

Postprandial maximum increase of blood glucose in rat

| Group | Postprandial maximum increase of blood glucose (maximum increase value from initial value, relative value based on 100 for control group) |
|---|---|
| Control group | 100 ± 2.42 |
| Test group 1 (addition of 0.075 µg per g body weight of cycloartenol) | 92.03 ± 3.16 |
| Test group 2 (addition of 0.15 µg per g body weight of cycloartenol) | 79.74 ± 7.71* |

TABLE 1-continued

Postprandial maximum increase of blood glucose in rat

| Group | Postprandial maximum increase of blood glucose (maximum increase value from initial value, relative value based on 100 for control group) |
|---|---|
| Comparative group (addition of 0.15 µg per g body weight of 24-methylenecycloartanol) | 89.25 ± 4.32 |

As shown in Table 1, it was revealed that the postprandial increase of blood glucose tended to be decreased by the addition of 0.075 µg per g body weight of cycloartenol, and was significantly inhibited by the addition of 0.15 µg per g body weight of cycloartenol, showing that cycloartenol exhibits an effect of inhibiting the postprandial increase of blood glucose. Further, it was revealed that the effect of cycloartenol was stronger than that of 24-methylenecycloartanol.

The invention claimed is:

1. A method of improving postprandial hyperglycemia in a human being or other animal, comprising administering or ingesting an amount of cycloartenol or an ester or glycoside derivative of cycloartenol sufficient to inhibit the postprandial increase of blood glucose that occurs after ingestion of carbohydrate by said human being or said animal wherein said cycloartenol or derivative thereof is administered or ingested with food or up to 30 minutes before food intake, and wherein said food comprises carbohydrate.

2. The method of improving postprandial hyperglycemia according to claim 1, wherein said method comprises orally administering or ingesting 50 µg to 500 mg per day of cycloartenol.

3. The method of improving postprandial hyperglycemia according to claim 1, wherein said cycloartenol or a derivative thereof is a purified cycloartenol or a derivative thereof.

4. The method of claim 2, wherein 100 µg to 20 mg per day of cycloartenol is administered or ingested.

5. The method of claim 1, wherein said cycloartenol is administered or ingested during food intake.

6. The method of claim 1, wherein said cycloartenol is administered or ingested 5 to 30 minutes before food intake.

7. The method of claim 1, wherein said cycloartenol is administered or ingested orally.

8. The method of claim 7, wherein said cycloartenol that is administered or ingested is in the form of a tablet, a capsule, a granule, a powder, or a syrup.

9. The method of claim 1, wherein said cycloartenol is administered parenterally.

10. The method of claim 9, wherein said cycloartenol is administered by injection, suppository, inhalant or transdermally.

11. The method of claim 1, wherein said cycloartenol is in combination with a food.

12. The method of claim 1, wherein said cycloartenol is in combination with a pharmaceutically acceptable excipient.

13. The method of claim 1, wherein said cycloartenol is administered to or ingested by said human being.

14. The method of claim 1, wherein said cycloartenol is administered to or ingested by said animal.

* * * * *